United States Patent [19]

Kakimoto et al.

[11] Patent Number: 4,837,022

[45] Date of Patent: Jun. 6, 1989

[54] COMPOSITION CONTAINING TISSUE PLASMINOGEN ACTIVATOR

[75] Inventors: Fumio Kakimoto; Naoki Asakawa, both of Gifu; Yasuo Ishibashi, Gifu; Yasuo Miyake, Aichi, all of Japan

[73] Assignee: Eisai Co., Ltd., Tokyo, Japan

[21] Appl. No.: 905,402

[22] Filed: Sep. 10, 1986

[30] Foreign Application Priority Data

Sep. 10, 1985 [JP] Japan .............................. 60-198629
Nov. 22, 1985 [JP] Japan .............................. 60-261397

[51] Int. Cl.$^4$ ........................................... A61R 37/547
[52] U.S. Cl. ................................ 424/94.3; 424/94.1; 424/94.64; 435/212; 435/215; 435/217; 435/188; 514/21; 514/970; 530/354
[58] Field of Search ................. 514/21; 530/350, 354; 424/94.1, 94.3; 435/212, 215, 188, 217

[56] References Cited

U.S. PATENT DOCUMENTS

| | | | |
|---|---|---|---|
| 4,530,905 | 7/1985 | Freedman | 530/354 |
| 4,552,760 | 11/1985 | Murakami et al. | 424/95 |
| 4,568,544 | 2/1986 | Hasegawa et al. | 435/216 |
| 4,604,379 | 8/1986 | Iwardowski et al. | 530/354 |
| 4,659,570 | 4/1987 | Terano | 530/251 |
| 4,661,469 | 4/1987 | Sarnoff | 514/2 |
| 4,714,754 | 12/1987 | Namiki et al. | 530/354 |
| 4,749,689 | 6/1988 | Miyata et al. | 530/354 |
| 4,777,043 | 10/1988 | Bennett et al. | 424/94.64 |

OTHER PUBLICATIONS

Murakami et al., CA vol. 104, 1986, #213259u.
Murakami et al., CA vol. 102, 1985 #58407d.

*Primary Examiner*—Delbert R. Phillips
*Assistant Examiner*—Garnette D. Draper
*Attorney, Agent, or Firm*—Wenderoth, Lind & Ponack

[57] ABSTRACT

A composition containing a tissue Plasminogen Activator (tPA) which comprises a partial hydrolyzate of gelatin cross-linked to a diisocyanate as an essential ingredient; or alternatively a partial hydrolyzate of gelatin cross-linked to a diisocyanate and one or more of a basic amino acid or salt thereof. The composition enhances the solubility of the tPA in water, thereby making the tPA further available in the treatment of circulatory diseases caused by thrombi.

11 Claims, 2 Drawing Sheets

COMPOSITION CONTAINING TISSUE PLASMINOGEN ACTIVATOR

BACKGROUND OF THE INVENTION

1. Field of the Invention

This invention relates to a composition containing a tissue plasminogen activator. Namely, this invention is available in medical fields. More particularly, it relates to a composition which has been invented for an improved application of a tissue plasminogen activator, which is employed to treat various circulatory diseases caused by thrombosis, to medical fields. 2. Description of Prior Arts According to custom, tissue plasminogen activator will be hereinafter abbreviated as tPA.

It is well known that thrombi can be dissolved by adenolysis with the use of a group of compounds called tissue plasminogen activators to thereby relieve circulatory disorders caused thereby. That is to say, active plasmin formed by a plasminogen activator destroys fibrin network and dissolves the same. Conventionally available plasminogen activators for therapeutic uses include streptokinase and urokinase. However these compounds are not specific to thrombi but may sometimes destroy not only fibrin but also blood proteins such as fibrinogen, prothrombin and factors V and VIII accompanied by some side effects including internal hemorrhage. Therefore streptokinase and urokinase are directly administered to a thrombus via a catheter, which requires a troublesome procedure. Thus the administration of those compounds has been on the decline. On the other hand, there are some plasminogen activators extracted from normal and cancerous tissues. These plasminogen activators are classified into urokinase plasminogen activator (uPA) and tissue plasminogen activator (tPA), which relates to the present invention, depending on the origins.

It is known that tPA is therapeutically useful since it has a much higher affinity for fibrin than uPA does. Thus it has been urgently required to establish a pharmaceutical technique to fully utilize the excellent therapeutic effect of tPA as described above.

Since, however, tPA is a protein hardly soluble in water, it is very difficult to formulate the same into an aqueous preparation such as an injection. It is the most serious problem in the practical application of tPA in medical fields. tPA should be directly administered to the circulatory system so that it can not be practically applied unless thoroughly solubilized in water. However there has been no satisfactory technique for the dissolution of tPA in water. Prior art concerning a tPA preparation includes the one disclosed in Japanese Patent Laid-Open No. 196824/1984. However the problem of the dissolution of tPA in water is not solved thereby.

SUMMARY OF THE INVENTION

Under these circumstances, we have examined various techniques for improving the solubility of tPA in water. As a result, we have found that the addition of a partial hydrolyzate of gelatin cross-linked to a diisocyanate brings about a remarkable improvement in the solubility of tPA in water.

Further, we have found that the solubility of tPA in water is synergistically increased by means of a combination use of (i) a partial hydrolyzate of gelatin cross-linked to a diisocyanate (hereinafter referred to hydrolyzate of gelatin) and (ii) one or more of a basic amino acid or a salt thereof.

Accordingly, it is an object of the present invention to improve the solubility of tPA in water.

Another object of this invention is to provide a composition containing a tPA, which comprises the hydrolyzate of gelatin.

A further object of this invention is to provide a composition containing a tPA, which comprises the hydrolyzate of gelatin, and one or more of a basic amino acids or salts thereof.

DETAILED DESCRIPTION OF THE PREFERRED EMBODIMENTS

Figure 1:
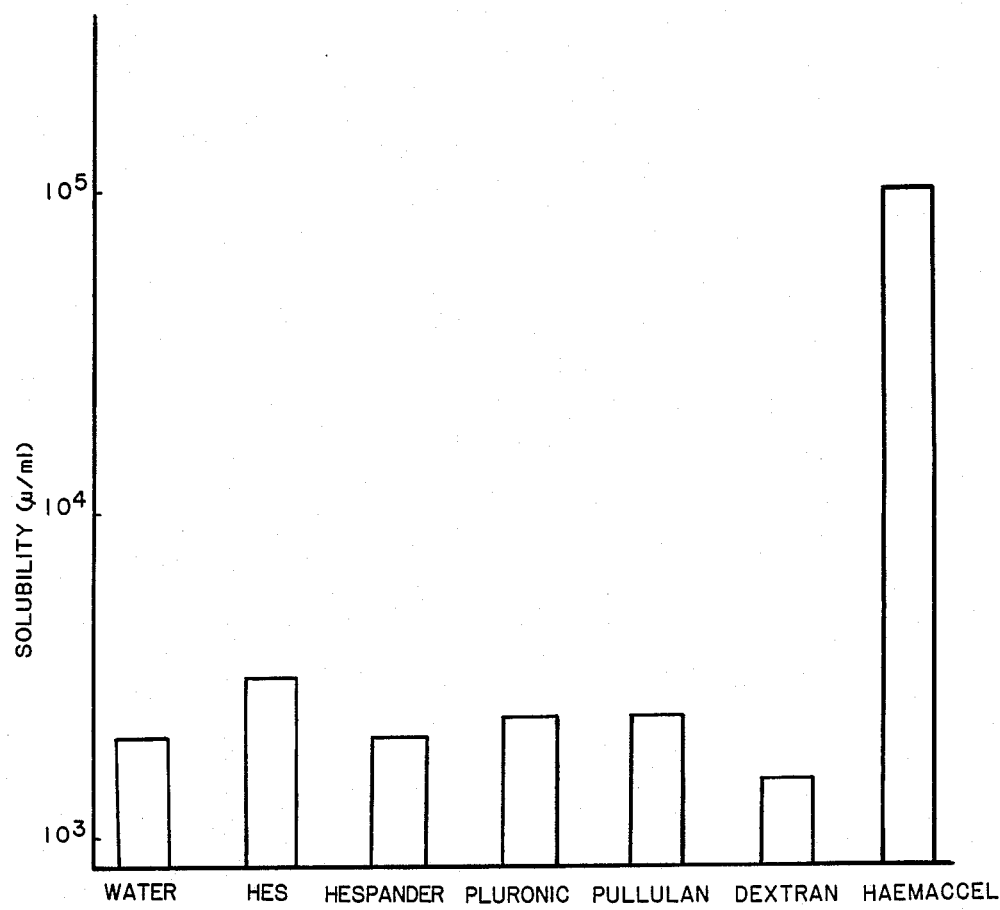
FIG. 1 is a bar graph showing the solubilities of tPA in water and in aqueous solutions each containing an additive.

Now the present invention will be described in detail. In the present invention, tPA may be either one extracted from natural sources or one obtained from microorganisms or cells artificially prepared through bio-engineering techniques. Thus anything generally available and used as a human plasminogen activator may be employed in the present invention regardless of its origin.

The partial hydrolyzate of gelatin cross-linked to a diisocyanate of the present invention is, more particularly, a substitute for plasma having no anti-genicity which is obtained by partially hydrolyzing gelatin to give a low molecular polypeptide and binding this polypeptide to a diisocyanate. The one having an average molecular weight of 35,000, i.e., haemaccel mfd. by Hoechst may be employed. This compound is described in detail in German Pat. No. 1118792 and No. 1155134.

As will be shown in Experimental Examples hereinbelow, the solubility of tPA increases with an increase in the concentration of this substance. Therefore the concentration of this substance as well as that of tPA in the composition of the present invention are not restricted. However it should be not that an excessively high concentration of this substance makes the resulting aqueous solution highly viscous and difficult to handle. Thus it is preferable that this substance is incorporated in the composition of the present invention to give a concentration of at most 10%, more preferably at most 5%, in the final aqueous solution.

As a basic amino acid to be used with the present invention, there may be mentioned, for example, arginine, ornithine, lysine, and hystidine. And, the salts of these basic amino acids may include salts of inorganic acid such for example as hydrochloride, or salts of organic acids such as acetate, asparagate, or glutamate.

Basic amino acids and the salts thereof influence on an osmotic pressures of the aqueous solutions. Depending on the increase of the concentration of basic amino acids and the salts thereof, the corresponding osmotic pressures will increase accordingly. In a viewpoint of administration to a living body, therefore, it is generally preferable to incorporate an amount so that the aqueous solution may form the concentration of 1-5%. There may be used, if necessary, a less amount or an excess amount than the above-mentioned amount of a basic amino acid.

The composition of the present invention may further contain other ingredients such as fillers, stabilizers, buffers and isotonic agents without departing from the spirit of the invention. It is to be understood that the present invention is not limited thereby. For example, the composition of the present invention may contain any sugars and amino acids and formulated into a lyophilized preparation.

The composition of the present invention is mainly in the form of an aqueous solution. However those previously prepared to formulate an aqueous solution are also included therein.

Examples of the preparation of the composition are as follows.

(i) tPA and a partial hydrolyzate of gelatin bound to a diisocyanate, which will be referred to as the additive of the invention, are present together in the same aqueous solution.

(ii) An aqueous solution containing tPA and another one containing the additive of the invention are separately prepared in a form of kit, and mixed together prior to the use.

(iii) A powder of tPA is prepared by, for example, lyophilization. Separately an aqueous solution of the additive of the present invention is prepared. These materials are mixed together prior to the use.

(iv) A powder of tPA is prepared by, for example, lyophilization. Separately a powder of the additive of the present invention is prepared by, for example, lyophilization. These are mixed together prior to the use in a appropriate aqueous solution, which may be combined with the above materials.

The composition of the present invention may be prepared in a conventional manner depending on the desired form. For example, an aqueous solution of tPA is pipetted into vials and lyophilized therein to give vials each containing a tPA powder. Separately an aqueous solution of the additive of the present invention is pipetted in vials. These materials are combined together to give the composition of the present invention.

The above consideration may be similarly applied to a composition containing a tPA, which comprises the hydrolyzate of gelatin and one or more of a basic amino acid or a salt thereof.

More particularly, the medical composition of the present invention relates not only to a solid composition or an aqueous composition which comprises containing altogether tPA and hydrolyzate of gelatin as well as one or more of a basic amino acid or a salt thereof, but also to a kit-type composition wherein a moiety portion of tPA and the other moiety portion of the hydrolyzate of gelatin and a basic amino acid and/or a salt thereof are individually prepared, such for example as, in one hand, a vial containing a lyophilized tPA powder such an injection preparation to be instantly used, and on the other hand, an ampule for a dissolution which contains an aqueous solution of the hydrolyzate of gelatin and a basic aminobasic acid and/or a salt thereof.

The following experiment shows the confirmation as to the effect for proving the improved enhancement of solubility of tPA by virtue of a combination of tPA and the hydrolyzate of gelatin and a basic amino acid or a salt thereof.

Respective 1,000 U of sample of tPA are pipetted into small test tubes. There are added into each of the tubes 50 μl of an aqueous solution containing the partial hydrolyzate (average molecular weight : 35,000) of gelatin cross-linked to hexamethylene diisocyanate and/or a certain basic amino acid hydrochloride or water (as control). The whole is thoroughly mixed, followed by subjecting to a centrifuge. The predetermined amount of the supernatant is taken up. The test sample is diluted with 0.1 M trishydrochloride buffer (pH 8) containing BSA, followed by determing tPA activity in accordance with Fibrin-plate Method [T. Astrup : Arch. Biochem. Biophys 40, 346 (1952)]. The results are shown in the following Table 1.

TABLE 1

Improved effect of solubility of tPA by virtue of a combination of a partial hydrolyzate of gelatin and a basic amino-acid hydrochloride
(tPA activity: U/ml)

| Amount of addition of a basic amino-acid (%) | Amount of addition of a partial hydrolyzate of gelatin cross-linked to hexamethylene diisocyanate (%) | |
|---|---|---|
| | 0 | 5 |
| Control (Water) 0 | 2,100 | 107,000 |
| Arginine hydrochloride 2 | 60,000 | 280,000 |
| Arginine hydrochloride 5 | 180,000 | 399,000 |
| Ornithine hydrochloride 2 | 130,000 | 244,000 |
| Lysine hydrochloride 2 | 130,000 | 195,000 |
| Hystidine hydrochloride 2 | 55,000 | 162,000 |

From Table 2, it is apparently proved that combination uses of a partial hydrolyzate of gelatin cross-linked to hexamethylene diisocyanate and a salt of a basic aminoacid exhibit remarkably improved effects with respect to solubility of tPA, as compared with a single use of control (water only), or a partial hydrolyzate of gelatin cross-linked to hexamethylene diisocyanate, a salt of a basic aminoacid.

The present invention is effective in enhancing the solubility of tPA in water to thereby provide an aqueous solution of tPA of a high concentration. A particular example thereof is an injection of a high tPA titer. As will be shown in Experimental Examples hereinbelow, the solubility of tPA in water represented in titer unit (u) in the absence of the partial hydrolyzate of gelatin cross-linked to a diisocyanate is 2144 u/ml while those obtained by adding 1%, 2.5%, 5% and 10 5 of said additive are 34042 u/ml, 598345 u/ml, 106923 u/ml and 138038 u/ml, respectively. Thus a remarkable effect of enhancing the solubility is observed.

To further illustrate the present invention, the following Examples will be given.

EXAMPLE 1

An aqueous solution containing 10 g of a partial hydrolyzate of gelatin cross-linked to a diisocyanate, 10 g of mannitol and 10,000,000 unit of tPA in 100 ml of a 0.03 M phosphate buffer solution of pH 7.5 was prepared under a sterile condition. 1-ml portions of this solution were pipetted in vials, lyophilized and sealed.

Separately, ampules each containing 2 ml of distilled water for injection were prepared by dissolution.

Example 2

10,000,000 unit of tPA powder prepared under a sterile condition was homogeneously mixed with 10 g of sterile mannitol and the mixture was packed in vials in an amount of 100,000 unit per vial and sealed.

Separately a solution containing 10 g of a partial hydrolyzate of gelatin cross-linked to a diisocyanate in 200 ml of a 0.01 M phosphate buffer solution (pH 7.5) was prepared under a sterile condition. 2-ml portions of this solution were pipetted in ampules to thereby give dissolution ampules.

Example 3

An aqueous solution containing 10 g of a partial hydrolyzate of gelatin cross-linked to a diisocyanate and 4 g of glycine in 100 ml of a 0.03 M phosphate buffer solution was prepared under a sterile condition, lyophiized and ground to give a powder. To the obtained powder, 10,000,000 unit of tPA powder was added and the mixture was packed in vials in an amount of 100,000 unit of tPA per vial and sealed.

Separately ampules each containing 2 ml of distilled water for injection were prepared for dissolution.

The following Experimental Examples will be given to illustrate the effects of the present invention.

Experimental Example 1

1000 u portions of tPA were introduced into small test tubes and 50-ul portions of water or 5% aqueous solutions of the following additives (1) to (6) were added thereto:
(1) hydroxyethylstarch (HES),
(2) low substituted hydroxyethylstarch (Hespander),
(3) ethylene oxide/propylene oxide copolymer (Pluronic),
(4) pullulan,
(5) dextran, and
(6) partial hydrolyzate of gelatin cross-linked to a diisocyanate (Haemaccel).

After thoroughly mixing and centrifuging each mixture, a given amount of the supernatant was recovered and diluted with a 0.1M tris hydrochloride buffer solution (pH 8, containing BSA). Thus the tPA activity was determined with the use of a fibrin plate.

FIG. 1 shows the result. FIG. 1 is a bar graph which shows the solubility (u/ml) of tPA in water or in an 5% aqueous solution of each additive.

FIG. 1 suggests that the addition of the partial hydrolyzate of gelatin cross-linked to a diisocyanate significantly enhances the solubility of tPA in water.

Experimental Example 2

The same procedure as the one described in Experimental Example 1 was performed except that the 5% aqueous solutions of the additives (1) to (6) were replaced by 1%, 2.5%, 5%, and 10% aqueous solutions of Haemaccel. Thus the relationship between the concentration of aqueous solutions of Haemaccel and the solubility of tPA in water was examined.

Figure 2:
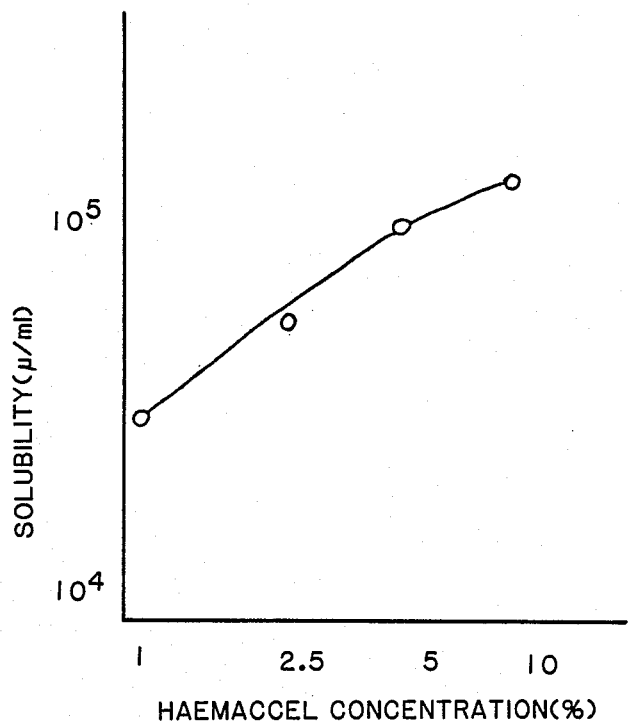
FIG. 2 is a graph showing the relationship between the concentration of an aqueous solution of Haemaccel and the solubility of tPA in said solution.

Table 2 and FIG. 2 show the result.

FIG. 2 is a graph which shows the solubility (u/ml) of tPA in aqueous solutions of Haemaccel of various concentrations. FIG. 2 suggests that the solubility of tPA in water increases with an increase in the concentration of the partial hydrolyzate of gelatin cross-linked to a diisocyanate.

TABLE 2

| Haemaccel concentration (%) | tPA solubility (μ/ml) |
| --- | --- |
| 1 | 34042 |
| 2.5 | 59845 |
| 5 | 106923 |
| 10 | 138038 |

Example 4

An aqueous solution containing 2 g of L-arginine hydrochloride, 5 g of a partial hydrolyzate of gelatin cross-linked to hexamethylene diisocyanate (average molecular weight : 35,000) and 10,000,000 unit of tPA in 100 ml of a 0.03 M phosphate buffer solution of pH 7.5 was prepared under a sterile condition. 1-ml portions of this solution were pipetted in vials lyophilized and sealed.

Separately, ampules each containing 2 ml of distilled water for injection were prepared for dissolution.

When the present injection preparation is used, the content of ampule for dissolution is added into the vial, and the whole is mixed altogether, resulting in a homogeneous aqueous solution containing 100,000 units of tPA. This solution has the concentration of the partial hydrolyzate of gelatin of 2.5% (W/V), and the concentration of L-arginine hydrochloride of 1% (W/V).

Example 5

An aqueous solution containing 1.6 g of L-ornithine hydrochloride, 5 g of a partial hydrolyzate of gelatin cross-linked to hexamethlene diisocyanate and 10,000,000 unit of tPA in 100 ml of a 0.03 M phosphate buffer solution of pH 7.5 was prepared under a sterile condition.

1-ml portions of this solution were pipetted in vials, lyophilized and sealed.

Separately, ampules each containing 2 ml of distilled water for injection were prepared for dissolution.

Example 6

An aqueous solution containing 2 g of L-hystidine hydrochloride, 5 g of a partial hydrolyzate of gelatin cross-linked to hexamethylene diisocyanate and 10,000,000 unit of tPA in 100 ml of a 0.03 M phosphate buffer solution of pH 7.5 was prepared under a sterile condition. 1-ml portions of this solution were pipetted in vials, lyophilized and sealed.

Separately, ampules each containing 2 ml of distilled water for injection were prepared for dissolution.

Example 7

An aqueous solution containing 1.6 g of L-lysine hydrochloride, 5 g of a partial hydrolyzate of gelatin cross-linked hexamethylene diisocyanate, and 10,000,000 unit of tPA in 100 ml of a 0.03 M phosphate buffer solution of pH 7.5 was prepared under a sterile condition. 1-ml portions of this solution were pipetted in vials, lyophilized, and sealed.

Separately, ampules each containing 2 ml of distilled water for injection were prepared for dissolution.

Example 8

An aqueous solution containing 3 g of L-arginine asparagate, 5 g of a partial hydrolyzate of gelatin cross-linked to hexamethylene diisocyanate, and 10,000,000 unit of tPA in 100 ml of a 0.03 M phosphate buffer solution of pH 7.5 was prepared under a sterile condition. 1-ml portions of this solution were pipetted in vials, lyophilized, and sealed.

Separately, ampules each containing 2 ml of distilled water for injection were prepared for dissolution.

Example 9

An aqueous solution containing 2.6 g of L-lysine asparagate, 5 g of a partial hydrolyzate of gelatin cross-linked to hexamethylene diisocyanate, and 10,000,000 unit of tPA in 100 ml of a 0.03 M phosphate buffer solution of pH 7.5 was prepared under a sterile condition. 1-ml portions of this solution were pipetted in vials, lyophilized, and sealed.

Separately, ampules each containing 2 ml of distilled water for injection were prepared for dissolution.

Example 10

An aqueous solution containing 0.8 g of L-arginine, hydrochloride, 1.2 g of L-hystidine hydrochloride, 5 g of a partial hydrolyzate of gelatin cross-linked to hexamethylene diisocyanate, and 10,000,000 unit of tPA in 100 ml of a 0.03 M phosphate buffer solution of pH 7.5 was prepared under a sterile condition. 1-ml protions of this solution were pipetted in vials, lyophilized and sealed.

Separately, ampules each containing 2 ml of distilled water for injection were prepared for dissolution.

Example 11

1.8 g of L-arginine and 5 g of a partial hydrolyzate of gelatin cross-linked to hexamethylene diisocyanate were dissolved in 70 ml of a distilled water for injection. The solution was adjusted by an addition of hydrochloric acid to pH of 7.0–8.0. 10,000,000 Unit of tPA was added to the solution to dissolve the former, followed by adding a distilled water for injection to make the total volume to 100 ml. The solution was sterilized and filtered. 1-ml portions of this solution were pipetted in vials, lyophilized and sealed.

Separately, ampules each containing 2 ml of distilled water for injection were prepared for dissolution.

Example 12

10,000,000 Unit of a sterilely prepared tPA powder and 4 g of a sterile mannitol are homogeneously mixed. The mixture is filled so that the tPA may be 100,000 unit per vial, and sealed.

Separately, a solution containing 4 g of L-arginine hydrochloride and 10 g of a partial hydrolyzate of gelatin cross-linked to hexamethylene diisocyanate in 200 ml of a 0.03 M phosphate buffer solution of pH 7.5 was prepared under a sterile condition. 2-ml protions of this solution were pipetted in vials, to prepare ampules for dissolution.

What is claimed is:

1. A composition containing a tissue Plasminogen Activator (tPA), which comprises a partial hydrolyzate of gelatin cross-linked to a diisocyanate as an essential ingredient in an amount sufficient to increase the solubility of the tissue Plasminogen Activator (tPA) in water.

2. A composition containing a tissue Plasminogen Activator (tPA), which comprises (1) a partial hydrolyzate of gelatin cross-linked to a diisocyanate (2) and one or more of a basic amino acid or a salt thereof said components (1) and (2) being present in amounts sufficient to increase the solubility of the tissue Plasminogen Activator (tPA) in water.

3. A composition containing a tissue Plasminogen Activator (tPA) as claimed in claim 1 or 2, wherein the composition is in a form of an aqueous solution or a preparation for producing an aqueous solution.

4. A composition containing a tissue Plasminogen Activator (tPA) as claimed in claim 1 or 2, wherein said partial hydrolyzate of gelatin cross-linked to a diisocyanate has an average molecular weight of 35,000.

5. A composition containing a tissue Plasminogen activator (tPA) as claimed in claim 2, wherein a basic amino acid is selected from the group consisting of arginine, ornithine, lysine and histidine, and a salt of a basic amino acid is an organic salt or an inorganic salt thereof.

6. A composition containing a tissue Plasminogen Activator (tPA) as claimed in claim 2, wherein an organic salt of a basic amino acid is acetate, asparagate or glutamate of a basic amino acid, and an inorganic salt of a basic aminoacid is hydrochloride of a basic aminoacid.

7. An aqueous composition containing a tissue Plasminogen Activator (tPA) as claimed in claims 1 or 2, wherein the partial hydrolyzate of gelatin is incorporated in a concentration of less than 105 in the aqueous solution.

8. An aqueous composition containing a tissue Plasminogen Activator (tPA) as claimed in claims 1 or 2, wherein the partial hydrolyzate of gelatin is incorporated in a concentration of less than 5% in the aqueous solution.

9. An aqueous composition containing a tissue Plasminogen Activator (tPA) as claimed in claim 2, wherein one or more of a basic amino acid is incorporated in a concentration of 1–5% in the aqueous solution.

10. An aqueous composition containing a tissue Plasminogen Activator (tPA) as claimed in claims 1 or 2, wherein a diisocyanate is hexamethylene diisocyanate.

11. An aqueous composition containing a tissue Plasminogen Activator (tPA) which comprises a partial hydrolyzate of gelatin cross-linked to a diisocyanate as an essential ingredient in an amount sufficient to increase the solubility of the tissue Plasminogen Activator (tPA) in water, but wherein the partial hydrolyzate of gelatin is present in a concentration of less than 10%, and containing one or more of a basic amino acid or a salt thereof in a concentration of 1–5%.

* * * * *